(12) United States Patent
Cowan et al.

(10) Patent No.: US 9,023,055 B2
(45) Date of Patent: May 5, 2015

(54) SURGICAL INSTRUMENT AND SURGICAL INSTRUMENT SYSTEM

(75) Inventors: Dean Cowan, Leeds (GB); Ian Leslie, Leeds (GB); Alberto Verteramo, Rome (IT)

(73) Assignee: Depuy (Ireland), Cork (IE)

( * ) Notice: Subject to any disclaimer, the term of this patent is extended or adjusted under 35 U.S.C. 154(b) by 201 days.

(21) Appl. No.: 13/636,219

(22) PCT Filed: Mar. 22, 2011

(86) PCT No.: PCT/GB2011/050567
§ 371 (c)(1),
(2), (4) Date: Nov. 30, 2012

(87) PCT Pub. No.: WO2011/117623
PCT Pub. Date: Sep. 29, 2011

(65) Prior Publication Data
US 2013/0131682 A1    May 23, 2013

(30) Foreign Application Priority Data
Mar. 24, 2010  (GB) .................................. 1004851.0

(51) Int. Cl.
   *A61B 17/15*      (2006.01)
(52) U.S. Cl.
   CPC ............. *A61B 17/157* (2013.01); *A61B 17/154* (2013.01); *A61B 17/155* (2013.01); *A61B 17/15* (2013.01)
(58) Field of Classification Search
   USPC .............................................. 606/87, 88, 102
   See application file for complete search history.

(56) References Cited

U.S. PATENT DOCUMENTS

| 4,524,766 | A  |   | 6/1985  | Petersen |
| 4,738,253 | A  | * | 4/1988  | Buechel et al. ................. 606/80 |
| 5,171,244 | A  |   | 12/1992 | Caspari |
| 8,414,653 | B2 |   | 4/2013  | Burstein et al. |
| 8,715,288 | B2 |   | 5/2014  | Cowan et al. |
| 2005/0085920 | A1 |   | 4/2005  | Williamson |
| 2007/0219559 | A1 | * | 9/2007  | Heavener et al. ............... 606/87 |

OTHER PUBLICATIONS

UK Search Report GB 1004851.0 dated Jul. 5, 2010.
PCT International Search Report PCT/GB2011/050567 dated Jul. 1, 2011.

(Continued)

*Primary Examiner* — Christopher Beccia

(57) ABSTRACT

A surgical instrument for attachment to a cutting block having a cutting slot defining a cutting plane is described. The surgical instrument comprises a dual purpose indicator (2) member. The indicator member is configured to (i) allow visualization of a first plane and (ii) to indicate a predetermined distance from a second plane perpendicular to the first plane. The surgical instrument also comprises an attachment member (14,16,18,20) for attaching the surgical instrument to the cutting slot in either of two mutually perpendicular orientations such that either the first plane or the second plane is parallel to the cutting plane. The surgical instrument can therefore be used both to visualize a plane of a cut and to indicate a distance from the plane of a cut, depending on the orientation of the attachment member in the cutting slot. This allows inventory to be reduced because the surgical instrument can replace two prior art instruments. The surgical instrument may form part of a system with one or more cutting blocks.

14 Claims, 2 Drawing Sheets

(56) References Cited

OTHER PUBLICATIONS

Measured Resection Fixed Reference Surgical Technique, DePuy Orthopaedics, Inc. and DePuy International Ltd., 2007 http://www.depuyknees.com|QuickLinksAttachments|Measured_Resection_Surg_Tech.pdf.

Japanese Search Report for Japanese Patent Application 2013-500587 dated Oct. 3, 2014, 2 pages.

* cited by examiner

SURGICAL INSTRUMENT AND SURGICAL INSTRUMENT SYSTEM

CROSS REFERENCE TO RELATED APPLICATION

This application is a National Stage 35 U.S.C. 371 of International Patent Application PCT/GB2011/050567 filed Mar. 22, 2011.

BACKGROUND OF THE INVENTION

The present invention relates to a surgical instrument and in particular to a surgical instrument having a dual purpose which is for attachment to a cutting block.

During knee surgery, cutting blocks are used to define positions of cuts. These cutting blocks include slots for receiving instruments for cutting and resection. It is known to provide instruments that attach to the cutting slot of a cutting block to indicate the height of a resection or to allow a plane of a cut to be visualised.

In knee surgery, the plane of a cut may be visualised using an instrument sometimes referred to as an "angel wing", "visualisation wing" or "resection guide" which inserts into the cutting slot. The angel wing is generally planar and enables the plane of the cut to be visualised by a surgeon.

At a different stage in the knee surgery procedure, the surgeon needs to set the superior/inferior height of the proximal tibial resection, using a tibial cutting block. In this case, a tibial stylus is inserted into the cutting slot of the tibial cutting block. The tibial stylus may include a pointer that can be adjusted to various different heights from the cutting slot to allow the surgeon to set the desired height or have a fixed pointer at a particular height.

It would be desirable to reduce the inventory and number of instruments required for knee surgery.

BRIEF SUMMARY OF THE INVENTION

The present invention provides a surgical instrument which can be used to both provide a visualisation of a plane of a cut and to set a height of a cut.

Accordingly, in a first aspect of the invention, there is provided a surgical instrument for attachment to a cutting block having a cutting slot defining a cutting plane, the surgical instrument comprising a dual purpose indicator member, wherein the indicator member is configured to (i) allow visualisation of a first plane and (ii) to indicate a predetermined distance from a second plane perpendicular to the first plane and an attachment member for attaching the surgical instrument to the cutting slot in either of two mutually perpendicular orientations such that either the first plane or the second plane is parallel to the cutting plane.

The present invention is based on the finding that although prior art "angel wings" and styli instruments are inserted into different cutting blocks at different stages in the procedure, the relationship between the planes of indication of the two types of instrument is perpendicular. This enables a dual purpose instrument to be provided, which can both allow visualisation of a first plane and indicate distance from a second plane, perpendicular to the first plane. Therefore, instead of two instruments, only one instrument is required, reducing the costs of instrumentation for the surgical procedure.

It should be noted that the surgical instrument of the present invention can be inserted into different types of cutting blocks, providing these have a cutting slot. For example, when visualising a plane, the instrument may be inserted into a different type of cutting block than when used to indicate a predetermined distance from a second plane perpendicular to the first plane.

Preferably, the dual purpose indicator member comprises a planar surface defining the first plane and a tip positioned a predetermined distance from the second plane which is perpendicular to the first plane. This form of indicator member enables it to perform the dual functions with a shape which is easy to form. In some embodiments, the dual purpose indicator member may simply be formed from a sheet, with the sheet providing the planar surface for visualisation of the first plane.

Preferably, the attachment member comprises a first tab extending in the first plane for insertion into the cutting slot and a second tab extending in the second plane for insertion into a cutting slot. These tabs can simply be inserted into a cutting slot to allow use of the instrument. The two tabs each extend in one of the planes in which the instrument works, thereby allowing it to be attached easily in the desired orientation. Preferably, the second tab extends in the same direction as the first tab, which is typically the direction defined by the line adjoining the first and second planes.

In one embodiment, the first and second tab are adjacent and spaced apart from each other. This ensures that when one tab is inserted into a cutting slot the other tab is sufficiently spaced apart from the tab in use such that it does not interfere with insertion of the tab into the cutting slot. This embodiment can be formed easily when the two tabs extend in the same direction defined by the line joining the first and second planes. In that case the adjacent and spaced tabs can be manufactured by removing material immediately adjacent the line joining the two planes, thereby creating tabs which are spaced apart and adjacent each other.

The surgical instrument may further comprise a second dual purpose indicator member configured to (i) allow visualisation of the first plane and (ii) to indicate a second predetermined distance from the second plane. This provides several advantages. The second dual purpose indicator member allows visualisation of the first plane from more positions of the instrument relative to the cutting slot. The second dual purpose indicator member can also be used to indicate a different distance from the second plane than the first dual purpose indicator member.

In this embodiment the attachment member preferably further comprises a third tab extending in the first plane for insertion into the cutting slot, wherein the third tab extends in the opposite direction from the first tab, and a fourth tab extending in the second plane for insertion into the cutting slot, wherein the fourth tab extends in the opposite direction from the second tab. The opposite direction may be the opposite direction along the line joining the first and second planes. In a preferable embodiment, the first and third tab are mirror symmetric with each other, and the second and fourth tab are mirror symmetric with each other.

In a preferable embodiment, the first predetermined distance is about 9 mm and the second predetermined distance is about 2 mm. In the prior art, a tibial stylus is adjustable to indicate different distances. However, it has been found that indication of 2 mm and 9 mm distances is sufficient for the majority of surgical procedures. This allows the construction of the instrument to be simplified because no need for adjustment to different distances is required. It will be appreciated that in other embodiments, different versions of the instrument may be provided indicating different distances, which are normally based on the construct thickness of the implant design.

In some embodiments, the attachment member may comprise at least one securing member for engaging the cutting slot. This can be helpful to ensure that the surgical instrument is held within the cutting slot and is less likely to move or fall out. A secure attachment to the cutting slot is particularly advantageous when the instrument is being used to indicate a distance in the second plane. It is therefore preferred that a securing member is provided on the second and/or fourth tab, if a fourth tab is present. The securing means may be formed by a resilient tang. This can be easily manufactured and provide sufficient force to secure the instrument by acting against the surface of the cutting slot.

The surgical instrument of the present invention can be manufactured by a number of techniques. These include injection moulding or forming from a single sheet of resilient material, such as a metal. Alternative methods of manufacturing include stamping or photoetching. The surgical instrument can therefore be formed in a single, integral piece. In other embodiments, the surgical instrument may comprise various different pieces attached to each other, for example by bonding, welding or any other suitable means of attachment.

In another aspect of the invention the surgical instrument defined above, with or without the optional features also discussed, forms part of a surgical instrument system. The surgical instrument system also comprises a cutting block having a cutting slot for use with the surgical instrument. In use the attachment member of the surgical instrument is inserted into the cutting slot.

In one embodiment the surgical instrument system is for use in knee surgery and includes a tibial cutting block and/or a femoral cutting block. If the system includes both tibial and femoral cutting blocks the attachment member may used to attach the surgical instrument to the tibial cutting block in a different orientation than to the femoral cutting block. This allows use of the same surgical instrument for different functions with the different cutting block. The cutting block may also comprise fixation holes. In use, the fixation holes may allow the cutting block to be fixed to a bone of a patient, for example to a tibia or a femur.

BRIEF DESCRIPTION OF THE DRAWINGS

Embodiments of the invention will now be described by way of example with reference to the accompanying drawings, in which.

DETAILED DESCRIPTION OF THE INVENTION

Figure 1:
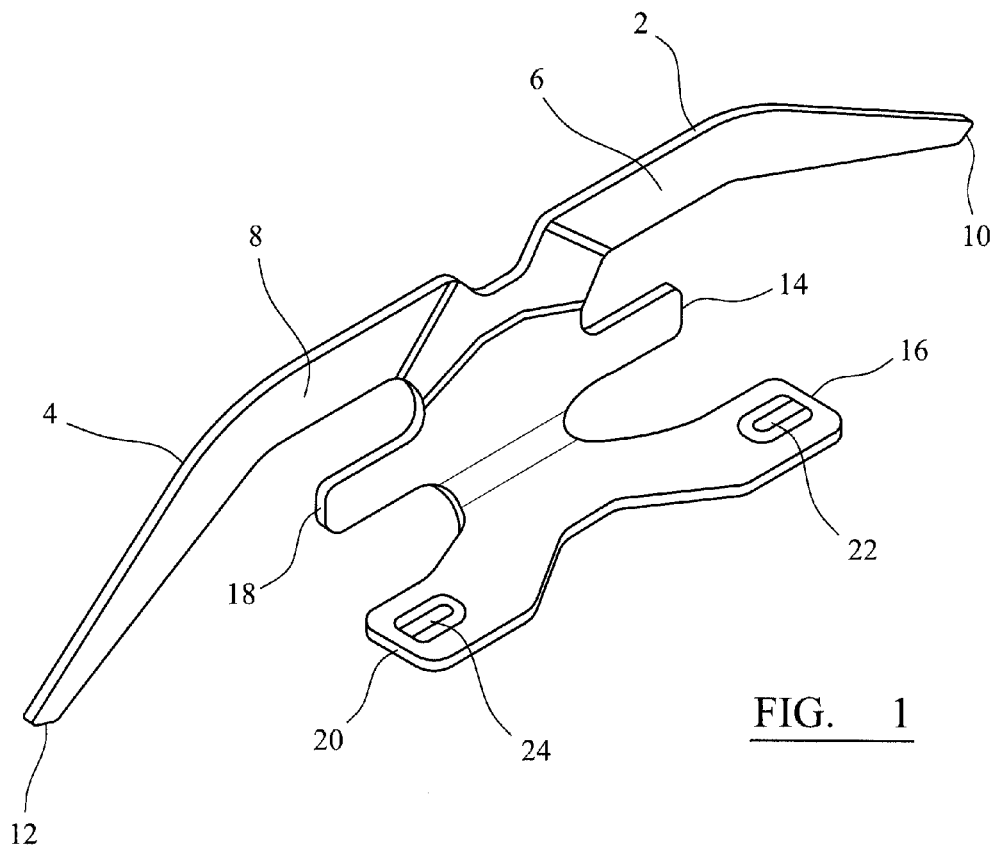
FIG. 1 depicts a perspective view of a first embodiment of the present invention.

FIG. 1 depicts a perspective view of a surgical instrument according to an embodiment of the present invention. The surgical instrument comprises a first dual purpose indicator member 2, a second dual purpose indicator member 4 extending in the opposite direction to the first dual purpose indicator member 2 and an attachment member joining the two dual purpose indicator members 2, 4. Each of the dual purpose indicator members 2, 4 include a planar surface 6, 8 for visualising a plane of a cut. The dual purpose indicator members 2, 4 each also comprise a tip 10, 12 for indicating a predetermined distance above a second plane, which is perpendicular to the plane of the planar surfaces 6, 8.

The attachment member comprises four tabs 14, 16, 18, 20. Tab 14 and tab 18 extend in a plane parallel to the plane of planar surfaces 6 and 8. Tabs 16 and 20 extend in a plane perpendicular to the plane indicated by planar surfaces 6 and 8, such that the tip 10, 12 of the dual purpose indicator members 2, 4 indicates a predetermined distance from the plane of tab 16 and tab 20.

Both of tabs 16 and 20 include a resilient tang 22, 24. This is bent slightly out of the plane of the tabs 16, 20. When the tab 16 or 20 is inserted into a cutting slot the resilient tang 22, 24 deforms elastically to bear against the surface of the cutting slot holding the surgical instrument in place more securely.

Figure 2:
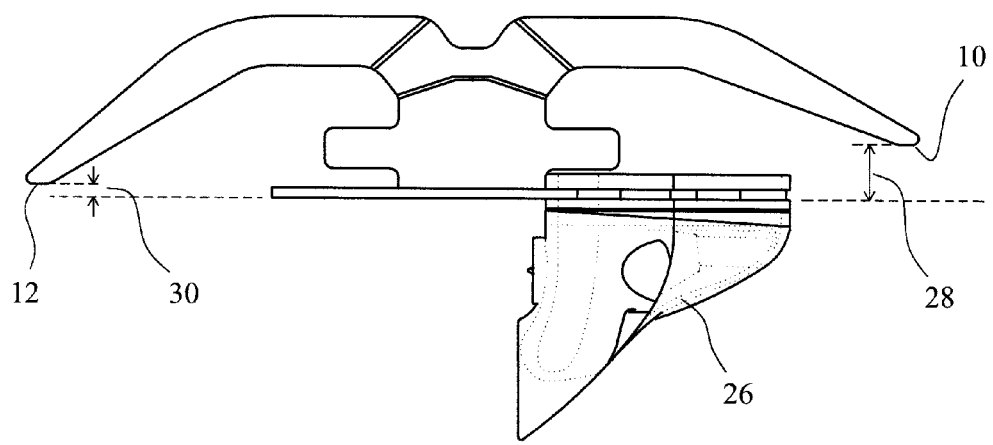
FIG. 2 is a side view of the instrument depicted in FIG. 1 functioning as a tibial stylus in combination with a tibial cut block.

FIG. 2 depicts a side view of the surgical instrument of FIG. 1 with tab 16 inserted into the cutting slot of a tibial cut block 26. As can be seen clearly in FIG. 2, the tip 10 of first dual purpose indicator number 2 is further from the second plane defined by the tabs 16, 20 than the tip 12 of the second dual purpose indicator member 4. In this embodiment tip 10 is about 9 mm from the plane (indicated by distance 28 in FIG. 2). Tip 12 of second dual purpose indicator number 4 is about 2 mm from the plane defined by tabs 16, 20 (indicated by distance 30 in FIG. 2). Thus, depending on whether tab 16 or tab 20 is inserted into the slot of the cutting block 26, the surgical instrument can be used as a stylus to indicate a distance of either 9 mm or 2 mm from the plane of the cutting slot.

In use, the tab 16 or tab 20 is held securely in the cutting slot by the action of the resilient tang 22, 24 acting against the surface of the cutting slot. Each of tabs 16 and 20 is narrower in width than the width of the cutting slot in tibial cutting slot 26. This enables the tip 10, 12 to be moved relative to the cutting block by both translation and rotation, so that the distance at various points relative to the cut block can be indicated.

Figure 3:
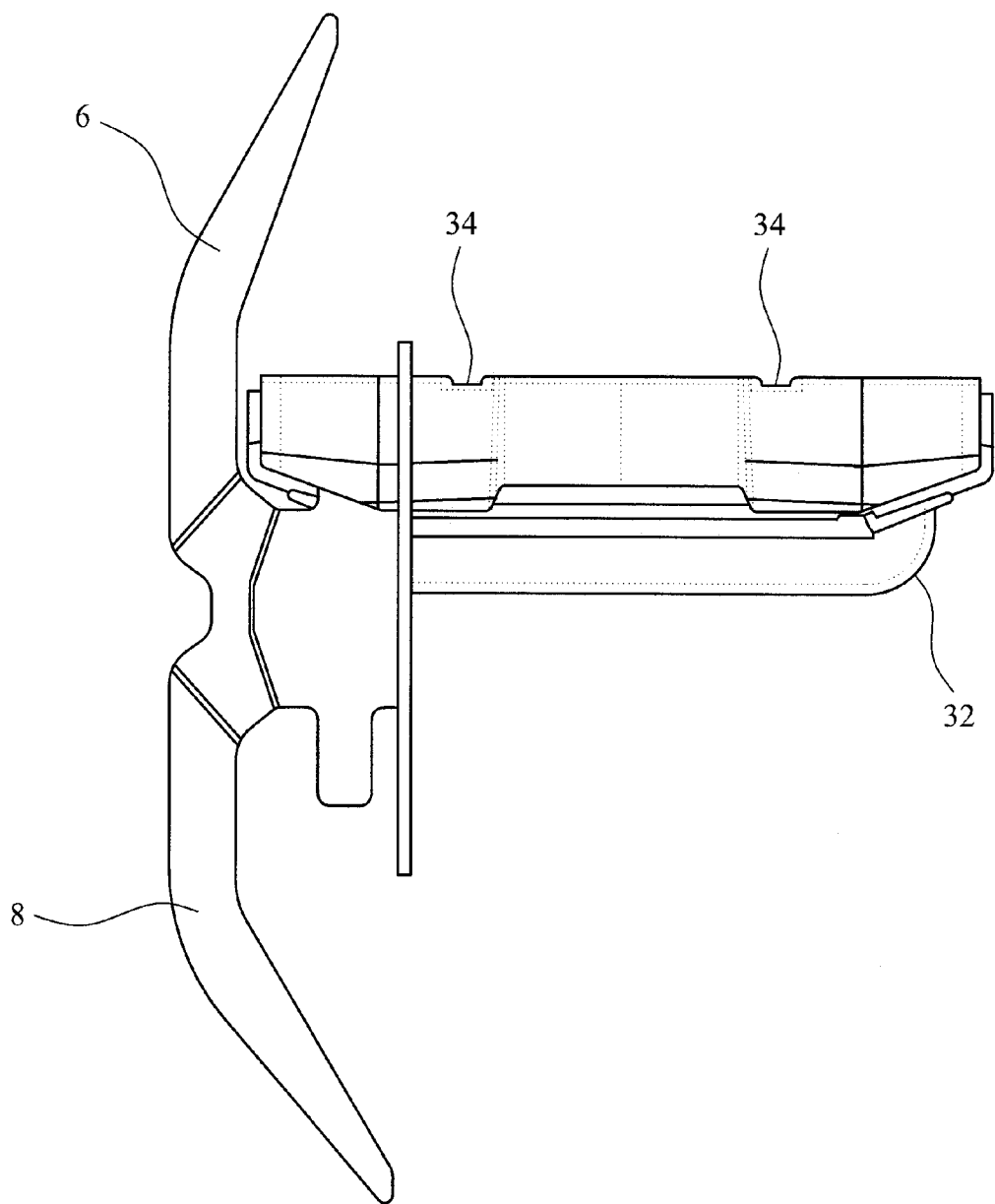
FIG. 3 depicts a side view of the instrument of FIG. 1 used to visualise the plane of a cut in combination with a femoral cut block.

FIG. 3 depicts a side view of the surgical instrument installed in a cutting slot of a femoral cut block 32. The femoral cut block also defines fixation holes for attachment to a femur. The entrance 34 to the fixation holes can be seen as slight recess in FIG. 3. The femoral cut block 32 is standard femoral cut block conventionally used in knee surgery with four cutting slots: two chamfer, one posterior and one anterior. Together these slots allow a shape to be cut to receive the femoral component in knee surgery. In this use, the surgical instrument is inserted into the anterior slot of the femoral cut block 32. It enables visualisation of a plane of the anterior cut to be made using the femoral cut block 32. The plane of the cut is indicated by the planar surface 6, 8 of the dual purpose indicator members. In this use, either tab 14 or tab 18 is inserted into the cutting slot. The planar surface 6 or 8 is then parallel with the plane defined by the slot of the cut block 32. Depending on whether tab 14 or tab 18 is inserted into the cutting slot of the cut block, the instrument can be used to visualise the plane of the cut on both the medial and lateral side.

As will be appreciated from FIGS. 2 and 3 when one of the tabs 14, 16, 18 or 20 are inserted into a cutting slot of a cut block, the presence of the perpendicular, adjacent tags could interfere with insertion into the cutting slot. For this reason, the space between tabs 14 and 16 and between tabs 18 and 20 is cut away along a line defined where the planes of the tabs meet. This ensures that when tab 16 or 20 is inserted into a cutting slot (as shown in FIG. 2) tabs 14 and 18 are sufficiently spaced that they do not contact the cutting block (as clearly depicted in FIG. 2). Likewise, when tabs 14, 18 are inserted into a cutting slot of a cut block, tabs 16 and 20 are sufficiently spaced that they do not interfere with the cutting block.

The surgical instrument of this embodiment is preferably formed from metal, so that it can be formed with sufficient strength and stiffness while maintaining a relatively thin profile of the tabs 14, 16, 18, 20 (approximately 1-2 mm thick). Any medical grade metal or metal alloy may be used, such as stainless steel. In alternative embodiments, a polymer may be used.

In alternate embodiments the distance of tips 10 and 12 on the plane defined by tabs 16 and 20 may be other than 2 and 9 mm. For example, the instrument may form part of a kit, with a number of instruments provided, indicating different pairs of measurements. In one embodiment these pairs are 1 and 10 mm, 2 and 9 mm, 3 and 8 mm, 4 and 7 mm and 5 and 6 mm. The combination of 2 and 9 mm is preferred when only a single instrument is supplied because it applies to a large number of surgical procedures.

In alternate embodiments, the dual purpose indicator member may have other forms than that depicted in FIG. 1, providing that it includes a planar surface to enable visualisation of the plane and a tip to enable indication of a distance from a plane perpendicular to the planar surface.

The invention claimed is:

1. A surgical instrument for attachment to a cutting block having a cutting slot defining a cutting plane, the surgical instrument comprising:
   a dual purpose indicator member, wherein the indicator member is configured to (i) allow visualisation of a first plane and (ii) to indicate a first predetermined distance from a second plane perpendicular to the first plane; and
   an attachment member for attaching the surgical instrument to the cutting slot in either of two mutually perpendicular orientations such that either the first plane or the second plane is parallel to the cutting plane;
   wherein the attachment member comprises:
      a first tab extending in the first plane for insertion into the cutting slot; and
      a second tab extending in the second plane for insertion into the cutting slot.

2. The surgical instrument of claim 1, wherein the dual purpose indicator member comprises:
   a planar surface defining the first plane; and
   a tip positioned a predetermined distance from the second plane, the tip being perpendicular to the first plane.

3. The surgical instrument of claim 1, wherein the first and second tab are adjacent and spaced from each other.

4. The surgical instrument of claim 1, further comprising:
   a second dual purpose indicator member configured to (i) allow visualisation of the first plane and (ii) to indicate a second predetermined distance from the second plane.

5. The surgical instrument of claim 4, wherein the attachment member further comprises:
   a third tab extending in the first plane for insertion into the cutting slot, wherein the third tab extends in the opposite direction from the first tab; and
   a fourth tab extending in the second plane for insertion into the cutting slot, wherein the fourth tab extends in the opposite direction from the second tab.

6. The surgical instrument of claim 4, wherein the first predetermined distance is about 9 mm and the second predetermined distance is about 2 mm.

7. The surgical instrument of claim 1 wherein the attachment member comprises at least one securing member for engaging the cutting slot.

8. The surgical instrument of claim 7, wherein the at least one securing member comprises a resilient tang.

9. The surgical instrument of claim 1, wherein the dual purpose indicator member and the attachment member are integrally formed.

10. A surgical instrument system comprising:
    a cutting block having a cutting slot defining a cutting plane; and
    a surgical instrument having a dual purpose indicator member, wherein the indicator member is configured to (i) allow visualisation of a first plane and (ii) to indicate a predetermined distance from a second plane perpendicular to the first plane, the surgical instrument further comprising an attachment member detachably attached to the cutting slot in either of two mutually perpendicular orientations such that the first plane or the second plane is parallel to the cutting plane;
    wherein the attachment member comprises:
       a first tab extending in one plane for insertion into the cutting slot; and
       a second tab extending in a plane perpendicular to the plane of the first tab for insertion into the cutting slot.

11. The surgical instrument system of claim 10, wherein the cutting block is a tibial cutting block.

12. The surgical instrument system of claim 10, wherein the cutting block is a femoral cutting block.

13. The surgical instrument system of claim 11, further comprising a femoral cutting block having a cutting slot defining a cutting plane.

14. The surgical instrument system of claim 10, wherein the cutting block further comprises fixation holes.

* * * * *